United States Patent [19]

Lam et al.

[11] Patent Number: 5,326,754
[45] Date of Patent: Jul. 5, 1994

[54] ANTITUMOR ANTIBIOTIC BMY-41219

[75] Inventors: Kin S. Lam, Cheshire, Conn.; Leonard A. McDonald, Salt Lake City, Utah; Jacqueline Mattei, Branford, Conn.; Salvatore Forenza; James A. Matson, both of Cheshire, Conn.

[73] Assignee: Bristol-Myers Squibb Co., New York, N.Y.

[21] Appl. No.: 63,383

[22] Filed: May 18, 1993

Related U.S. Application Data

[63] Continuation of Ser. No. 830,969, Feb. 6, 1992, which is a continuation of Ser. No. 764,114, Sep. 23, 1991, abandoned, which is a continuation of Ser. No. 489,431, Mar. 6, 1990, abandoned.

[51] Int. Cl.⁵ .................... C07D 273/00; A61K 31/00
[52] U.S. Cl. .......................................... 514/42; 514/43; 435/85; 435/87; 536/27.1
[58] Field of Search ................ 536/27.1; 514/42, 43; 435/85, 87

[56] References Cited

U.S. PATENT DOCUMENTS

| | | | |
|---|---|---|---|
| 4,487,925 | 12/1984 | Nettleton, Jr. et al. | 536/27.1 |
| 4,524,145 | 6/1985 | Matson et al. | 514/43 |
| 4,552,842 | 11/1985 | Nettleton, Jr. et al. | 435/75 |
| 4,567,143 | 1/1986 | Matson et al. | 435/119 |
| 4,785,085 | 11/1988 | Kaneko et al. | 536/27.1 |
| 4,808,613 | 2/1989 | Kaneko et al. | 514/42 |
| 5,158,938 | 10/1992 | Lam et al. | 514/42 |

Primary Examiner—Ronald W. Griffin
Assistant Examiner—James O. Wilson
Attorney, Agent, or Firm—Sandra M. Nolan

[57] ABSTRACT

An antitumor antibiotic designated BMY-41219 is produced by fermentation of *Saccharothrix aerocolonigenes* ATCC 39243. The BMY-41219 antibiotic exhibits antitumor activity.

1 Claim, 5 Drawing Sheets

ANTITUMOR ANTIBIOTIC BMY-41219

This application is a continuation of application Ser. No. 07/830,969 filed Feb. 6, 1992, which is a continuation of application Ser. No. 07/764,114 filed Sep. 23, 1991, now abandoned which was a continuation of application Ser. No. 07/489,431 filed Mar. 6, 1990, also abandoned.

BACKGROUND OF THE INVENTION

1. Field of the Invention

The invention is directed to the production of an antitumor antibiotic designated herein as BMY-41219 and to a process for the preparation, isolation and purification of BMY-41219.

2. Background Art

U.S. Pat. Nos. 4,487,925 and 4,552,842 disclose the anti-tumor agent designated rebeccamycin, and the 5'-methyl and 5',2',3", 6"-tetraacetate derivatives thereof, and a process for producing the same agent by cultivating a rebeccamycin-producing strain of *Nocardia aerocolonigenes*, preferably *Nocardia aerocolonigenes* ATCC 39243, or a rebeccamycin-producing mutant thereof in an aqueous nutrient medium containing assimilable sources of carbon and nitrogen under submerged aerobic conditions until a substantial amount of rebeccamycin is produced. Recently *Nocardia aerocolonigenes* ATCC 39243 was reclassified as *Saccharothrix aerocolonigenes* ATCC 39243 (Bush et. al., *J. Antibiotics* 40: 668–678, 1987).

It was found that when the rebeccamycin-producing culture was supplemented with L-tryptophan, the production of a minor analog of rebeccamycin was significantly enhanced. This analog of rebeccamycin was subsequently isolated and designated as BMY-41219.

SUMMARY OF THE INVENTION

The present invention provides a method for the production of an analog of the antitumor agent designated rebeccamycin (Formula I) in the fermentation of *Saccharothrix aerocolonigenes* ATCC 39243.

Formula I

More specifically, there is provided a method for the enhanced production of a rebeccamycin analog of the Formula II (BMY-41219) below, Formula II (BMY-41219)

as well as pharmaceutically acceptable acid addition salts of such analog.

The compound of the Formulas II is produced by supplementing the cultures of a rebeccamycin producing *Saccharothrix aerocolonigenes* with L-tryptophan.

DETAILED DESCRIPTION OF THE INVENTION

Figure 1A:
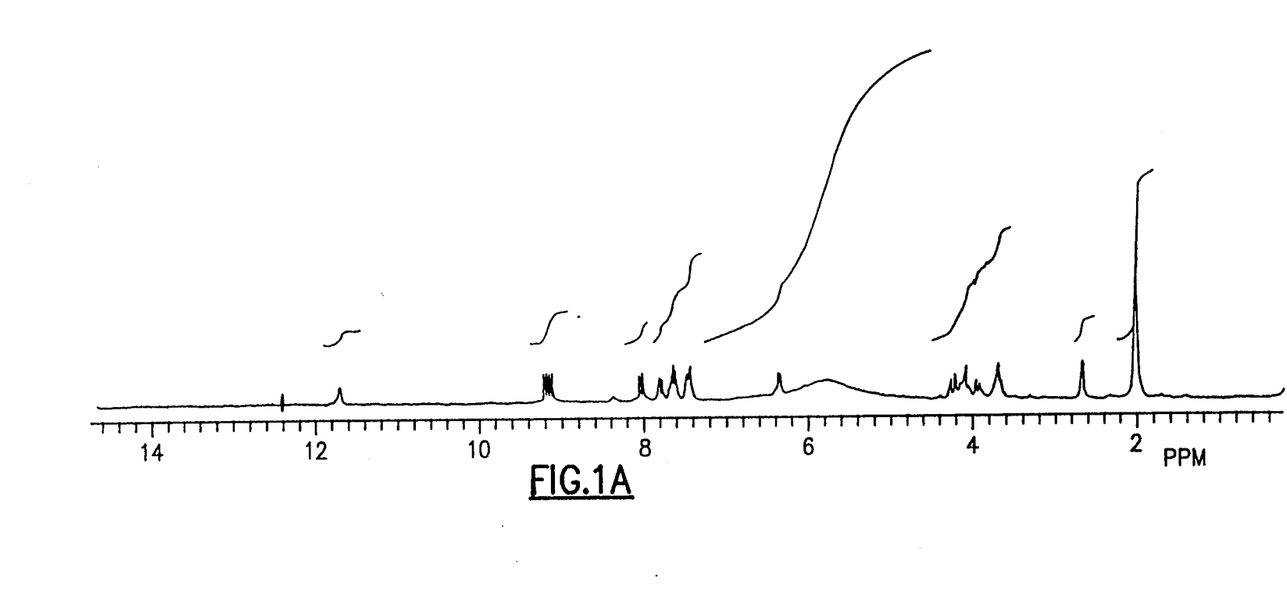
FIG. 1A shows the $^1$H-NMR for the compound of Formula II.
Figure 1B:
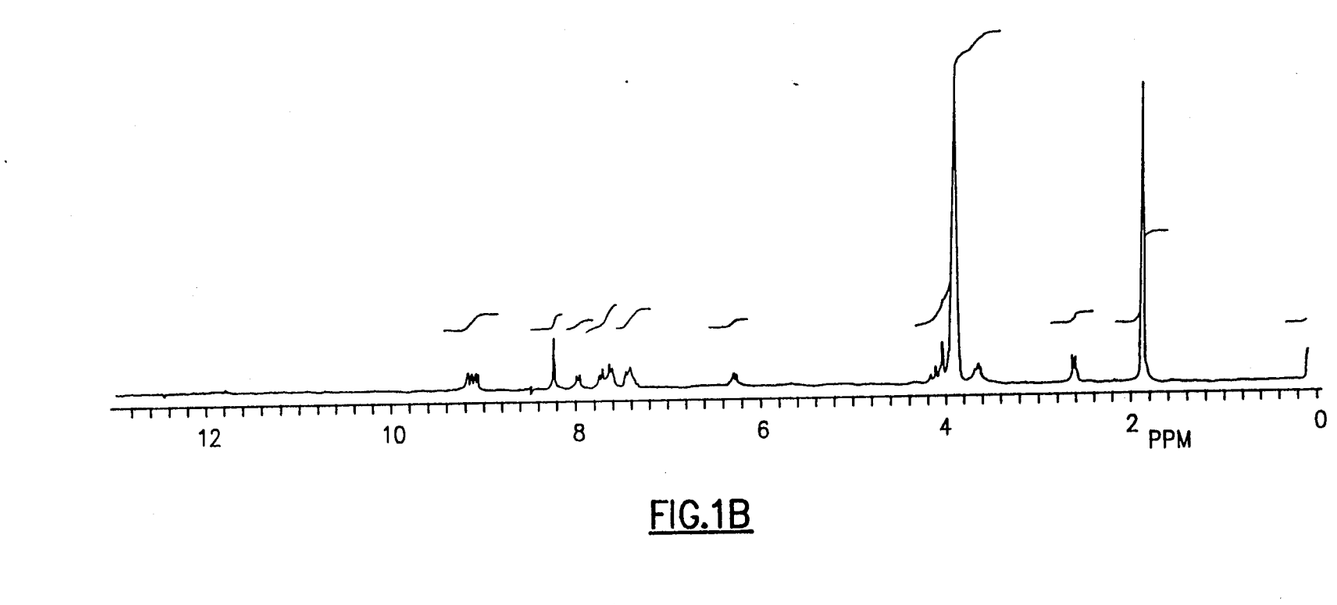
FIG. 1B shows the $D_2O$ exchange $^1$H-NMR for the compound of Formula II.
Figure 2A:
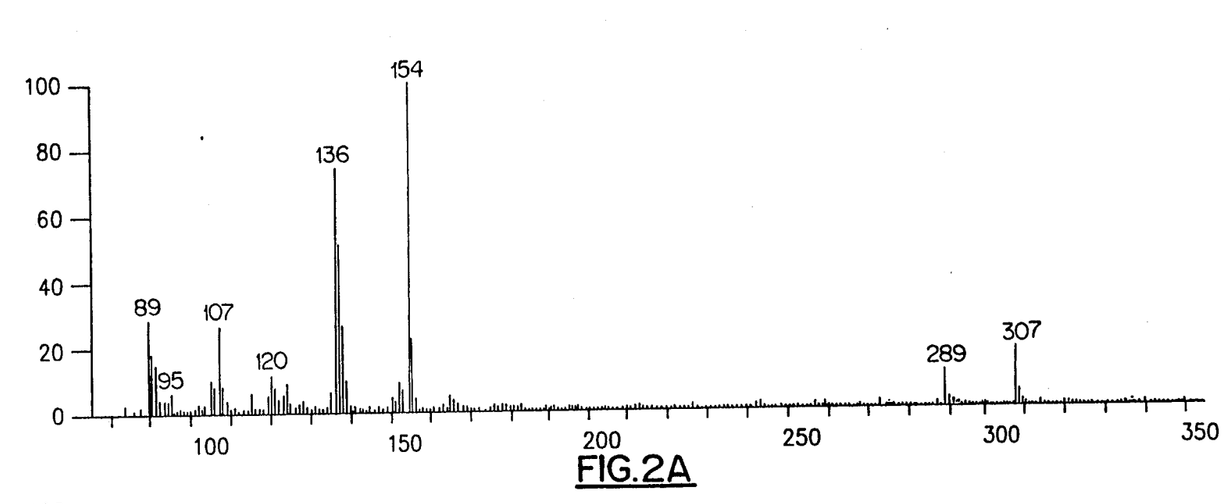
FIGS. 2A and 2B show the FAB-MS for the compound of Formula II (S=matrix NOBA).
Figure 2B:
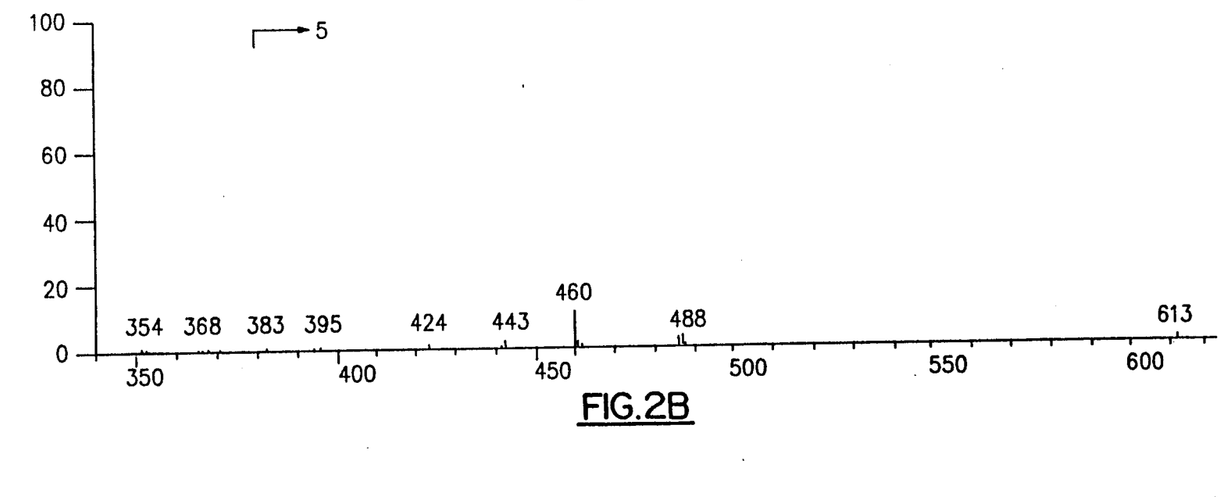
Figure 2C:
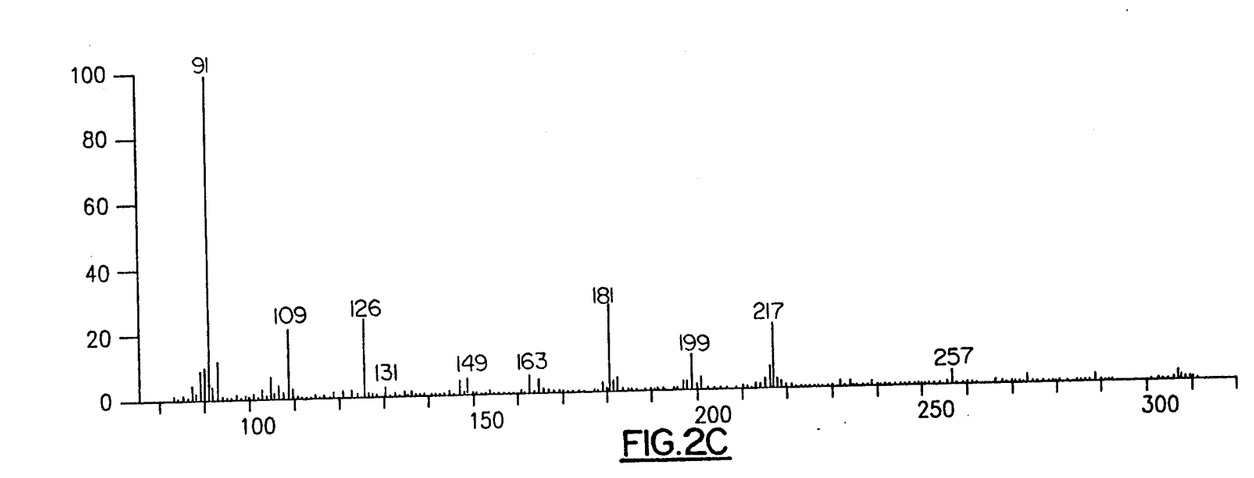
FIGS. 2C and 2D show the FAB-MS for the compound of Formula II (S=matrix thiogly.).
Figure 2D:
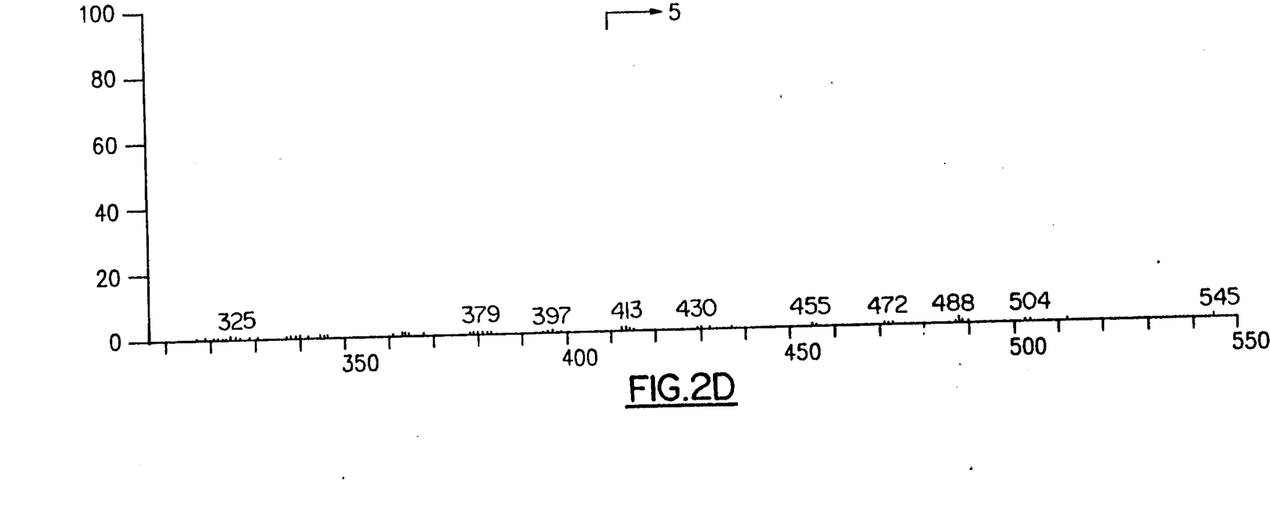
Figure 3:
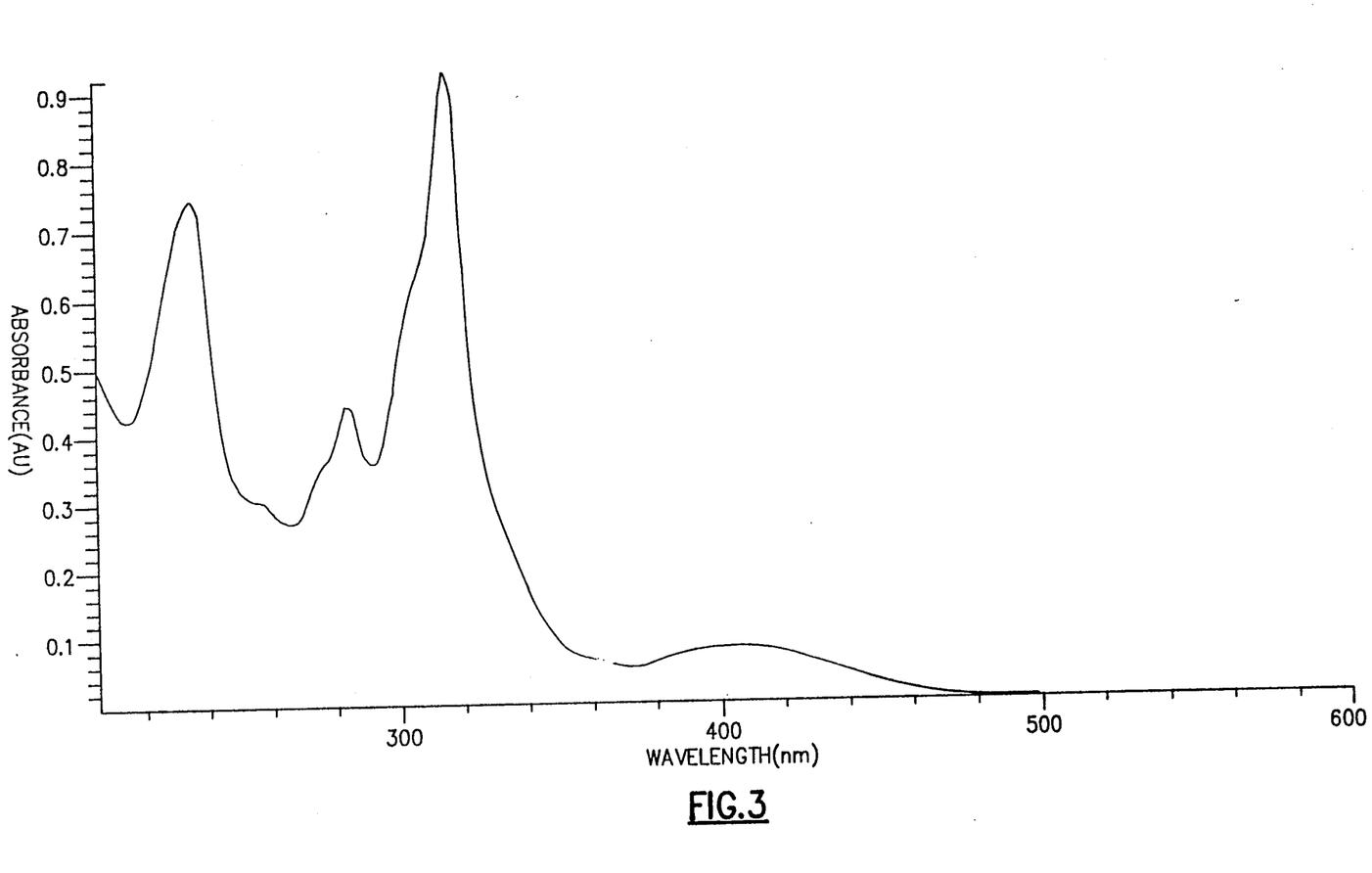
FIG. 3 shows the UV spectrum for the compound of Formula II.

U.S. Pat. Nos. 4,487,925 and 4,552,842 disclose the production and isolation of the antitumor agent designated rebeccamycin (Formula I)

Formula I

The above-mentioned rebeccamycin compound is the principal component of the fermentation of the rebeccamycin producing strain of *Nocardia aerocolonigenes*.

It has now been found according to the present invention that the fermentation procedure disclosed in U.S. Pat. Nos. 4,487,925 and 4,552,842 can be carried out in the presence of tryptophan to enhance the production of a analog of rebeccamycin having valuable antitumor properties. Rebeccamycin is still the principal component of the above fermentation. The rebeccamycin analog of the present invention has the Formula II below.

Formula II (BMY-41219)

Preparation of the Antibiotics

BMY-41219 is produced by cultivating a rebeccamycin producing strain of *Saccharothrix aerocolonigenes*, supplemented with L-tryptophan. The preferred producing organism is a novel strain of *Saccharothrix aerocolonigenes*, previously designated as *Nocardia aerocolonigenes* strain C38,383-RK2 (ATCC 39243) in U.S. Pat. No. 4,487,925. Recently, this strain was reclassified as *Saccharothrix aerocolonigenes* (Bush et. al., *J. Antibiotics* 40:668–678, 1987) and is designated herein as *Saccharothrix aerocolonigenes* strain C38, 383-RK2 (ATCC 392243). This strain was isolated from a soil sample collected in Panama. A biologically pure culture of strain C38,383-RK2 has been deposited with the American Type Culture Collection, Rockville, MD, and added to their permanent collection of microorganisms as ATCC 39243. This culture, designated as C38,383-RK2, is also maintained as a dormant culture in lyophile tubes and cryogenic vials in the Bristol-Myers Squibb Co. Pharmaceutical Research and Development Division Culture Collection, 5 Research Parkway, Wallingford, Conn. 06492.

The taxonomic studies on strain C38,383-RK2 (ATCC 39243) have been described in detail in U.S. Pat. No. 4,487,925 and in *J. Antibiotics* 40:668–678, 1987. The strain has been classified as a novel strain of *Saccharothrix aerocolonigenes*.

It is to be understood that the present invention is not limited to use of the particular preferred strain ATCC 39243 or to organisms fully answering its description. It is especially intended to include other rebeccamycin producing strains or mutants of the described organism which can be produced by conventional means such as x-radiation, ultraviolet radiation, treatment with nitrogen mustards, phage exposure and the like.

In practicing the present process, a rebeccamycin-producing strain of *Saccharothrix aerocolonigenes*, having the identifying characteristics of strain C38,383-RK2 (ATCC 39243), or a mutant or variant thereof, is cultivated in a conventional aqueous nutrient medium supplemented with L-tryptophan. The organism is grown in a nutrient medium containing known nutritional sources for actinomycetes. Thus, the organism is grown in a nutrient medium containing an assimilable carbon source such as sucrose, lactose, glucose, rhamnose, fructose, glycerol or soluble starch. The medium should also contain an assimilable nitrogen source such as fishemal, peptone, peanut meal, cottonseed meal, corn steep liquor, amino acids or ammonium salts. Nutrient inorganic salts can also be incorporated in the medium so as to provide sodium, potassium, ammonium, calcium, phosphate, sulfate, nitrate, carbonate and like ions. Trace elements such as copper, manganese, iron, zinc, etc. are added to the medium if desired, or they may be present as impurities of other constituents of the media. For optimal production of BMY-41219, the medium should be supplemented with L-tryptophan. Submerged aerobic conditions are preferably employed for the production of large quantities of antibiotic, although for production of limited amounts, surface cultures and bottles may also be used. The general procedures used for the cultivation of other actinomycetes are applicable to the present invention.

Production of the antibiotic of the present invention can be effected by any temperature conducive to satisfactory growth of the producing organism, e.g. 18° C. to 39° C. and is conveniently carried out at a temperature of about 28° C. The fermentation may be carried out in flasks or in laboratory or industrial fermentors of various capacity.

When tank fermentation is to be used it is desirable to produce a vegetative inoculum in a nutrient broth by inoculating a small volume of the culture medium with a slant, a cryopreservative culture or a lyophilized culture of the producing organism. After obtaining a viable and active inoculum in this manner, it is transferred aseptically to the fermentation tank charged with production medium for large scale production of the antibiotic of the present invention. The medium in which the vegetative inoculum is grown can be the same as, or different from, that utilized in the tank as long as it as such that a good growth of the producing organism is obtained and it is supplemented with L-tryptophan. Further agitation may be provided by a mechanical impeller. Antifoam agents such as lard oil or silicone oil may also be added if needed. Antibiotic production is monitored by high performance liquid chromatography assay or by conventional biological assay. In general, optimum production of the antibiotics of the present invention is achieved after incubation of about 10 days.

Isolation and purification of the so-obtained derivative may be carried out by conventional chromatographic procedures.

Physical and Chemical Properties

BMY-41219 has following Physical and Chemical Properties:

Description: Yellow-orange amorphous solid

Molecular Formula: $C_{26}H_{21}N_3O_7$

Molecular weight: 487

Mass Spectrum: FAB $(M+1)^+$ ion=488. Reference no. AT0702 and AT0703

Infrared Spectrum: KBr pellet major Bands (cm−1): 3600–2800, 3320, 3200, 2925, 1740, 1700, 1670, 1475, 1460, 1405, 1330, 1272, 1240, 1080, 1050, 1015, 910, 805, 750, 700, 655

Ultraviolet Spectrum: About 0.6 mg/50 ml MeOH. Absorption maximum (molar absorptivity): 236 nm (29975), 284 nm (17755), 316 nm (37418), 404 nm (3020).

Analytical HPLC: 10 uG in DMSO. k′—1.7. Column QBX C18. Eluant—4 parts 0.1 M Ammonium Acetate, 3 parts Methanol, 3 parts Acetonitrile. Flow—2.0 ml/min. Detector—315 nm.

200 MHz 1H-NMR: Varian XL-200. Solvent $d_6$-DMSO. Chemical Shifts (ppm): 11.70(s,1H), 9.17(d, 1H), 9.10(d, 1H), 7.97(d, 1H), 7.74(d, 1H), 7.57(m,2H), 7.37(m,2H), 6.28(d,H), 5.70(bs, exchangeable), 4.17-3.90(m,4H), 3.36(m,2H).

Solubility: Soluble in Dimethyl Sulfoxide, Methanol, and Tetrahydrofuran.

Biological Properties

BMY-41219 was tested against the transplanted mouse leukemia P388 to determine in vivo antitumor activity (Table 1). $CDF_1$ mice were implanted intraperitoneally (ip) with $10^6$ P388 leukemia cells obtained from DBA/2 donor mice bearing this transplantable murine leukemia. The $CDF_1$ leukemic mice were treated ip with either saline (control mice) or doses of BMY-41219 once at one day post-tumor inoculation. These animals were observed daily and their deaths recorded. Average body weight changes (from the day of leukemia implant to the day of last treatment) were determined for all groups as a means of reflecting drug toxicity. The incidence of mice alive in each group on Day 5 post-tumor implant was recorded as an additional means of assessing drug toxicity. No therapeutic result was considered as meaningful if more than one mouse per treatment group had died by Day 5. Each treatment group consisted of 6 mice; control groups contained 10 mice. The number of mice, if and, surviving to Day 30 (the last day of the experiment) was also recorded.

Therapeutic efficacy was evaluated by determining the median survival time (MST) of BMY-41219 treated mice and comparing it to the MST of parallel control mice. This comparison was made by dividing the MST of the former by the latter and multiplying by 100 to derive a parameter called the percent T/C value. A percent T/C of $\geq 125\%$ was considered to represent a meaningful increase in lifespan and hence an active result. As shown in Table 1, BMY-41219 is active against P388 leukemia at dose levels ranging from 7.5 to 240 mg/kg. The best effect was achieved at a dosage of 240 mg/kg and consisted of a %T/C of 170%. Toxicity was not observed even at the highest dose (240 mg/kg) tested.

TABLE 1

Effect of BMY-41219 on P388 leukemia[a]
(Day 1 treatment)

| Dose, ip (mg/kg/inj) | Medium Survival Times (Days) | % T/C | Average Weight Change (g) | No. of Mice Alive on Day 5 | No. of Mice Alive on Day 30 |
|---|---|---|---|---|---|
| 240 | 17.0 | 170 | 0 | 6/6 | 0/6 |
| 120 | 16.0 | 160 | 0.3 | 6/6 | 0/6 |
| 60 | 14.5 | 145 | 0.4 | 6/6 | 0/6 |
| 30 | 15.0 | 150 | 0.1 | 6/6 | 0/6 |
| 15 | 14.0 | 140 | 0.2 | 6/6 | 0/6 |
| 7.5 | 13.0 | 130 | 0.6 | 6/6 | 0/6 |
| Control | 10 | 100 | 2.4 | 10/10 | 0/10 |

[a]Mice were implanted with $10^6$ P388 leukemia cells and treatments with BMY-41219 were begun one day later. Control mice were given saline injections.

The present invention includes within its scope pharmaceutical compositions which comprise an effective tumor-inhibiting amount of BMY-41219 of the present invention, or a pharmaceutically acceptable acid addition salt thereof, in combination with an inert pharmaceutically acceptable carrier or diluent.

According to another aspect of the invention, a method is provided for therapeutically treating an animal (preferably mammalian) host effected by a malignant tumor which comprises administering to such host an effective tumor-inhibiting dose of the antibiotic of the present invention or a pharmaceutically acceptable acid addition salt thereof.

Examples of suitable compositions include solid compositions for oral administration such as tablets, capsules, pills, powders and granules, liquid compositions for oral administration such as solutions, suspensions, syrups and elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

It will be appreciated that the actual preferred dosages of the rebeccamycin analogs of the present invention will vary according to the particular compound being used, the particular composition formulated, the mode of application and the particular situs, host and disease being treated. Many factors that modify the action of the drug will be taken into account by those skilled in the art, e.g. age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by those skilled in the art using conventional dosage determination tests.

The present invention is illustrated by the following examples which are not intended to be construed as limiting the scope of the invention.

Example 1

Preparation of cryopreservative culture of *Saccharothrix aerocolonigenes* strain C38, 383-RK2 (ATCC 39243).

*Saccharothrix aerocolonigenes* strain C38,383-RK2 was maintained as a cryopreservative culture stored at $-80°$ C. in a Revco ultralow temperature freezer. To prepare a cryopreservative culture, strain C38,383-RK2 was transferred in test tubes on slants of yeast extract-malt extract agar supplemented with $CaCO_3$ which consisted of

| dextrose | 4.0 g |
| yeast extract | 4.0 g |
| malt extract | 10 g |
| $CaCO_3$ | 1.5 g |
| agar | 15 g |
| deionized water | q.s. to 1 liter |

The agar slant was incubated at 28° C. for 7–10 days. Vegetative culture was prepared by transferring the surface growth from the slant culture to a 500 ml Erlenmeyer flask containing 100 ml of a sterile vegetative medium consisting of

| Cerelose (Corn Products) | 30 g |
| Pharmamedia (Traders Oil Mill Co.) | 10 g |
| Nutrisoy (Archer Daniels Midland Co.) | 10 g |
| $CaCO_3$ | 3 g |
| deionized water | q.s. to 1 liter |

This vegetative culture was incubated at 28° C. for 48 hours on a rotary shaker set at 250 rev/min. The vegetative culture was mixed with equal volume of cryoprotective solution consisting of

| | |
|---|---|
| Sucrose | 100 g |
| glycerol | 200 g |
| deionized water | q.s. to 1 liter |

Four ml portions of this mixture were transferred to sterile cryogenic tube (5 ml capacity, Corning) and were frozen in a dry ice-acetone bath. The frozen vegetative cultures were then stored at −80° C. in a Revco ultralow temperature freezer.

Example 2.

Preparation of vegetative culture of *Saccharothrix aerocolonigenes* strain C38,383-RK2 (ATCC 39243).

Vegetative culture was prepared by transferring 4 ml of the cryopreservative culture to a 500 ml Erlenmeyer flask containing 100 ml of a sterile vegetative medium having the same composition as the vegetative medium described in Example 1. The vegetative culture was incubated at 28° C. for 48 hours on a rotary shaker set at 250 rev/min.

Example 3

Preparation of BMY-41219.

Four ml of the vegetative culture of Example 2 was inoculated into 500 ml Erlenmeyer flasks each containing 100 ml of a production medium consisting of

| | |
|---|---|
| Staclipse J-UB starch (A. E. Staley) | 60 g |
| Cerelose | 10 g |
| Nutrisoy | 10 g |
| Debittered Brewer's Yeast | 5 g |
| $FeSO_4.7H_2O$ | 1 g |
| $(NH_4)_2SO_4$ | 1 g |
| $NH_4H_2PO_4$ | 1 g |
| $CaCO_3$ | 10 g |
| deionized water | q.s. to 1 liter |

The production culture was incubated at 28° C. on a rotary shaker set at 250 rev/min. After 5 days of fermentation, L-tryptophan was added to the culture at a final concentration of 2 mg/ml. The culture was allowed to incubate at 28° C. and shaken at 250 rpm for additional 5 days. Production of BMY-41219 was monitored by HPLC. Optimal production of 119–155 mg/ml was generally obtained at 10 days of fermentation (i.e. 5 days after the addition of L-tryptophan).

Example 4

Isolation and purification of BMY-41219:
a) solvents and reagents

DICALITE Speedplus Diatomite filter aid was manufactured by GREFCO, INC. Torrance Calif. SEPHADEX LH20 was obtained from Pharmacia Fine Chemicals AB. Baker silica gel 7024-1 and Dimethyl Sulfoxide (DMSO) were obtained from the J. T. Baker Chemical Company. Ammonium Acetate and Acetonitrile were HPLC grade which were obtained from Fisher. Tetrahydrofuran and Methanol were HPLC grade which were obtained from American Burdick & Jackson. Chloroform, Hexane, and Ethyl Acetate were ACS reagent grade and were not re-distilled before use. The water used was in house de-ionized water which was passed through a Barnstead Nanopure II water purification system.

b) General Methods

The vacuum liquid chromatography (VLC) apparatus consists of a Kontes 250 ml medium porosity sintered glass funnel with side hose connection for vacuum and a T 24/40 joint for attachment to a receiving flask. The funnel was packed with dry silica which was equilibrated by drawing a volume of the least polar solvent (or solvent combination) in the elutropic series through the bed. The sample was adsorbed onto silica gel by dissolving it in an appropriate solvent, adding the adsorbent and, evaporating to dryness. The sample adsorbed silica gel was then transferred to the funnel as a least polar solvent (or solvent combination) slurry. Vacuum elution was carried out in a step gradient fashion from least polar to most polar. The bed of silica was sucked dry between each successive step of the gradient.

The following components were used to construct a semi-preparative high performance liquid chromatography (HPLC) system: Waters Associates model 590 Solvent Delivery System pump; Waters Associates model U6K injector with 2 ml loop; Whatman Partisil 10 ODS-3 (9.4mm i.d.×50 cm long) column; Knauer model 87 variable wavelength detector (320 nm); Heath model SR-204 strip chart recorder set at 0.2 in/min. The components were connected with 316 (1.6mm o.d. −0.23mm i.d.) stainless steel tubing. The eluant was pumped at 4.0 ml/min.

The following components were used to construct an analytical HPLC system: Waters Associates model 6000A Solvent Delivery System pump; Waters Associates U6K injector with a 2 ml loop; Q-BEX Scientific Incorporated C-18 (10 um, 3.9mm i.d.×30cm) column; Hewlett Packard Spectrophotometric Detector System consisting of the HP 1040A detector with DPU, the HP 85B computer, the HP 9121 disk drive, the HP 7470A plotter and, the HP THINKJET printer. The components were connected with 316 (1.6mm o.d −0.23mm i.d.) stainless steel tubing. The eluant was pumped at 2.0 ml/min.

Reversed phase thin layer chromatography (TLC) was carried out on Whatman reversed phase KC18F (20×20 cm) TLC plates. 2 ul samples were spotted and plates were developed in 60% Tetrahydrofuran 40% 0.1M ammonium acetate (V/V). The developed plates were air dried and visualized with 366 nmUV light.

c) Extraction and Purification

The whole broth (10 l) was filtered (admix) with 700 grams of Dicalite filter aid using a 12 inch Tollhurst Laboratory Centerslung Centrifugal Filter Unit (Amtek. INC., model 1B15) lined with a sewn filter bag coated with Dicalite filter aid. The mycelial mat was rinsed with 10 liters of water, removed from bag and, stirred with 6 liters of tetrahydrofuran for 2 hours. Filtration through a 24 cm Buchner funnel (Coors no. 11) fitted with a 24 cm S & S Sharkskin paper yielded a brown orange solution which was concentrated in-vacuo to a crude residue (37.4 g).

The Crude residue was tirturated with 2 liters of Chloroform and filtered through a Kimax 2000 ml-125C sintered glass funnel. The insoluble residue was further tirturated with 1 liter of Methanol and filtered through the Kimax funnel. Concentration in-vacuo, of the Methanol filtrate yielded 15.2 grams of RESIDUE A.

A 250 ml sintered glass funnel was packed with 66.2 grams of silica gel which was equilibrated with 50% Hexane Ethyl Acetate (V/V). RESIDUE A was dissolved in 50% Methanol 50% Tetrahydrofuran (V/V) to pre-adsorb it onto 25.8 grams of silica gel. The sample adsorbed silica gel was introduced to the equilibrated funnel as a 50% Hexane 50% Ethyl Acetate (V/V) slurry. Using pre-determined volumes and compositions of solvents, vacuum elution yielded eleven fractions as indicated below.

| FRACTION NUMBER | VOLUME ELUANT | ELUANT COMPOSITION (V/V) |
|---|---|---|
| 1 | 400 ML | 50% EtOAc 50% Hexane |
| 2 | 400 ML | 60% EtOAc 40% Hexane |
| 3 | 400 ML | 70% EtOAc 30% Hexane |
| 4 | 400 ML | 80% EtOAc 20% Hexane |
| 5 | 400 ML | 90% EtOAc 10% Hexane |
| 6 | 800 ML | 100% EtOAc |
| 7 | 400 ML | 99% EtOAc 1% Methanol |
| 8 | 400 ML | 95% EtOAc 5% Methanol |
| 9 | 800 ML | 90% EtOAc 10% Methanol |
| 10 | 400 ML | 100% Methanol |
| 11 | 500 ML | 100% Tetrahydrofuran |

Based upon the presence of a significant orange-yellow fluorescent zone (BMY-41219) on TLC analysis, fractions 5 through 8 were combined and evaporated in-vacuo to yield 131 mg of RESIDUE B.

RESIDUE B was dissolved in 3 ml Tetrahydrofuran and introduced onto a 2.5cm i.d.×70cm Glenco glass column which was packed with Sephadex LH20 swelled in Tetrahydrofuran (Bed Dimensions were 2.5cm×68cm). Elution with Tetrahydrofuran was carried out at 1.0 ml/min while 250 ml eluant was collected and discarded. Seventy 10 ml fractions were then collected and selectively surveyed by reversed phase TLC. Fractions 13 through 19 were shown by TLC to contain major amounts of BMY-41219 and were therefore combined and evaporated in-vacuo to yield 362mg of wet RESIDUE C.

A Whatman Partisil 10 column was equilibrated with a mobile phase consisting of 40% Tetrahydrofuran 60% 0.1M Ammonium Acetate at 4.0 ml/min. RESIDUE C was dissolved in 2 ml 50% Tetrahydrofuran 50% mobile phase and chromatographed in six 333 uL aliquots. A single fraction containing one peak at about 25 minutes was collected for each run. These six fractions were combined and evaporated in-vacuo to yield 132 mg BMY-41219.

What is claimed is:

1. A pharmaceutical composition for treating P388 leukemia comprising a tumor-inhibiting amount of the compound having the formula in combination with a pharmaceutical carrier.

* * * * *